US010011806B2

(12) United States Patent
Köhle et al.

(10) Patent No.: US 10,011,806 B2
(45) Date of Patent: Jul. 3, 2018

(54) METHOD FOR MAKING A TRIS-(2-HYDROXYETHYL)-METHYLAMMONIUM METHYLSULFATE FATTY ACID ESTER

(71) Applicant: Evonik Industries AG, Essen (DE)

(72) Inventors: Hans-Jürgen Köhle, Mainhausen (DE); Axel Euler, Flieden (DE); Kurt Seidel, Jossgrund (DE); Peter Schwab, Essen (DE)

(73) Assignee: Evonik Degussa GmbH, Essen (DE)

( * ) Notice: Subject to any disclaimer, the term of this patent is extended or adjusted under 35 U.S.C. 154(b) by 703 days.

(21) Appl. No.: 14/531,507

(22) Filed: Nov. 3, 2014

(65) Prior Publication Data

US 2015/0126431 A1    May 7, 2015

(30) Foreign Application Priority Data

Nov. 5, 2013  (EP) ..................................... 13191579

(51) Int. Cl.
| | | |
|---|---|---|
| *C07C 305/14* | (2006.01) |
| *C11D 3/00* | (2006.01) |
| *C07C 305/06* | (2006.01) |
| *C07C 213/08* | (2006.01) |
| *C07C 219/06* | (2006.01) |
| *C07C 219/08* | (2006.01) |
| *C11D 1/62* | (2006.01) |
| *C11D 3/20* | (2006.01) |
| *C11D 3/30* | (2006.01) |
| *C07C 303/24* | (2006.01) |

(52) U.S. Cl.
CPC ............ *C11D 3/001* (2013.01); *C07C 213/08* (2013.01); *C07C 219/06* (2013.01); *C07C 219/08* (2013.01); *C07C 303/24* (2013.01); *C07C 305/06* (2013.01); *C11D 1/62* (2013.01); *C11D 3/201* (2013.01); *C11D 3/30* (2013.01)

(58) Field of Classification Search
CPC ...... C11D 3/001; C07C 213/08; C07C 219/06
See application file for complete search history.

(56) References Cited

U.S. PATENT DOCUMENTS

| | | |
|---|---|---|
| 4,234,627 A | 11/1980 | Schilling |
| 4,514,461 A | 4/1985 | Woo |
| 4,747,880 A | 5/1988 | Berrido et al. |
| RE32,713 E | 7/1988 | Woo |
| 4,789,491 A | 12/1988 | Chang et al. |
| 4,882,220 A | 11/1989 | Ono et al. |
| 4,917,920 A | 4/1990 | Ono et al. |
| 4,954,285 A | 9/1990 | Wierenga et al. |
| 5,002,681 A | 3/1991 | Wierenga et al. |
| 5,137,646 A | 8/1992 | Schmidt et al. |
| 5,185,088 A | 2/1993 | Hartman et al. |
| 5,391,325 A | 2/1995 | Swenson et al. |
| 5,427,697 A | 6/1995 | Swartley |
| 5,474,691 A | 12/1995 | Severns |
| 5,476,599 A | 12/1995 | Rusche et al. |
| 5,480,567 A | 1/1996 | Lam et al. |
| 5,703,029 A | 12/1997 | Crass et al. |
| 5,759,990 A | 6/1998 | Wahl et al. |
| 5,792,219 A | 8/1998 | Hartman et al. |
| 5,827,451 A | 10/1998 | Cummings et al. |
| 5,830,845 A | 11/1998 | Trinh et al. |
| 5,877,145 A | 3/1999 | Wahl et al. |
| 5,916,863 A * | 6/1999 | Iacobucci ............... A61K 8/416 510/123 |
| 6,004,913 A | 12/1999 | Iacobucci et al. |
| 6,037,315 A | 3/2000 | Franklin et al. |
| 6,180,593 B1 | 1/2001 | Fender et al. |
| 6,180,594 B1 * | 1/2001 | Fender ..................... C11D 1/62 510/522 |
| 6,200,949 B1 | 3/2001 | Reijmer et al. |
| 6,235,914 B1 | 5/2001 | Steiger et al. |
| 6,255,274 B1 | 7/2001 | Becherer et al. |
| 6,376,455 B1 | 4/2002 | Friedli et al. |
| 6,458,343 B1 | 10/2002 | Zeman et al. |
| 6,492,322 B1 | 12/2002 | Cooper et al. |
| 6,608,024 B1 | 8/2003 | DuVal et al. |

(Continued)

FOREIGN PATENT DOCUMENTS

| | | |
|---|---|---|
| CA | 1312619 | 1/1993 |
| CS | 246532 | 3/1986 |

(Continued)

OTHER PUBLICATIONS

U.S. Appl. No. 15/517,220, filed Apr. 6, 2017, Köhle.
English translation of the International Search Report for international application PCT/EP2013/058427 (related to U.S. Appl. No. 14/398,962) filed Apr. 24, 2013.
English translation of the Written Opinion of the International Searching Authority for international application PCT/EP2013/058427 filed Apr. 24, 2013.
English translation of the International Preliminary Report on Patentability for international application PCT/EP2013/058427 filed Apr. 24, 2013.
European Search Report for EP 12 16 6976 (priority EP application of copending U.S. Appl. No. 14/398,962) filed May 7, 2012.
European Search Report for application EP 13 19 1579 (priority EP application of current U.S. Appl. No. 14/531,507) filed Nov. 5, 2013.
XP-002721964; English language abstract for JP 2013133547 dated Aug. 12, 2013.

(Continued)

*Primary Examiner* — Nicole M Buie-Hatcher
*Assistant Examiner* — M. Reza Asdjodi
(74) *Attorney, Agent, or Firm* — Law Office of Michael A. Sanzo, LLC

(57) ABSTRACT

In a method for making a tris-(2-hydroxyethyl)-methylammonium methylsulfate fatty acid ester by quaternizing a tris-(2-hydroxyethyl)-amine fatty acid ester with dimethylsulfate the quaternizing is carried out in the presence of a solid acid scavenger. The method can provide a fabric softener active composition, comprising from 65 to 98% by weight of at least one tris-(2-hydroxyethyl)-methylammonium methylsulfate fatty acid ester, the corresponding non-quaternized tris-(2-hydroxyethyl)-amine fatty acid esters in amounts providing a total amine number of the composition of from 2 to less than 7 mg KOH/g, and from 1 to 1500 ppm methanol.

20 Claims, No Drawings

(56) References Cited

U.S. PATENT DOCUMENTS

| | | |
|---|---|---|
| 6,645,479 B1 | 11/2003 | Shefer et al. |
| 6,653,275 B1 | 11/2003 | Fender et al. |
| 6,770,608 B2 | 8/2004 | Franklin et al. |
| 6,878,684 B2 | 4/2005 | Ellson et al. |
| 6,897,194 B2 | 5/2005 | Fan et al. |
| 6,987,074 B2 | 1/2006 | Ishii et al. |
| 6,995,131 B1 | 2/2006 | Frankenbach et al. |
| 7,572,761 B2 | 8/2009 | Gefvert |
| 7,704,940 B2 | 4/2010 | Boerefijn et al. |
| 7,994,110 B2 | 4/2011 | Wenk et al. |
| 8,183,199 B2 | 5/2012 | Fossum et al. |
| 8,361,953 B2 | 1/2013 | Nagy et al. |
| 8,507,425 B2 | 8/2013 | Schick et al. |
| 8,563,499 B2 | 10/2013 | Köhle et al. |
| 8,569,224 B2 | 10/2013 | Köhle et al. |
| 8,883,712 B2 | 11/2014 | Köhle et al. |
| 8,883,713 B2 | 11/2014 | Parrish et al. |
| 9,441,187 B2 * | 9/2016 | Kohle |
| 2002/0032146 A1 | 3/2002 | Schaumann et al. |
| 2003/0060390 A1 | 3/2003 | Demeyere et al. |
| 2003/0139313 A1 | 7/2003 | Turner et al. |
| 2003/0158344 A1 | 8/2003 | Rodrigues et al. |
| 2003/0165692 A1 | 9/2003 | Koch et al. |
| 2003/0195130 A1 | 10/2003 | Lentsch et al. |
| 2003/0195133 A1 | 10/2003 | Shefer et al. |
| 2003/0203829 A1 | 10/2003 | Shefer et al. |
| 2003/0215417 A1 | 11/2003 | Uchiyama et al. |
| 2003/0216282 A1 | 11/2003 | Martens et al. |
| 2003/0216488 A1 | 11/2003 | Uchiyama et al. |
| 2003/0220210 A1 | 11/2003 | DuVal et al. |
| 2004/0071742 A1 | 4/2004 | Popplewell et al. |
| 2004/0071746 A1 | 4/2004 | Popplewell et al. |
| 2004/0072719 A1 | 4/2004 | Bennett et al. |
| 2004/0072720 A1 | 4/2004 | Brain et al. |
| 2004/0087477 A1 | 5/2004 | Ness |
| 2004/0106536 A1 | 6/2004 | Mane et al. |
| 2004/0167056 A1 | 8/2004 | Lentsch et al. |
| 2004/0204337 A1 | 10/2004 | Corona et al. |
| 2005/0014672 A1 | 1/2005 | Arif |
| 2005/0032671 A1 | 2/2005 | Kvita et al. |
| 2006/0089293 A1 | 4/2006 | Frankenbach |
| 2006/0094639 A1 | 5/2006 | Martin et al. |
| 2006/0142175 A1 | 6/2006 | Haiss et al. |
| 2006/0252669 A1 | 11/2006 | Heibel et al. |
| 2006/0277689 A1 | 12/2006 | Hubig et al. |
| 2007/0054835 A1 | 3/2007 | Corona et al. |
| 2007/0066510 A1 | 3/2007 | Tee et al. |
| 2007/0179080 A1 * | 8/2007 | Gallotti .................. C11D 1/62 510/504 |
| 2007/0219111 A1 | 9/2007 | Ward et al. |
| 2008/0242584 A1 | 10/2008 | Wahl et al. |
| 2008/0263780 A1 | 10/2008 | Declercq et al. |
| 2008/0289116 A1 | 11/2008 | Young et al. |
| 2009/0124533 A1 | 5/2009 | Kottke et al. |
| 2009/0181877 A1 | 7/2009 | McGinnis et al. |
| 2011/0110993 A1 | 5/2011 | Chieffi et al. |
| 2011/0239377 A1 | 10/2011 | Fossum et al. |
| 2011/0239378 A1 | 10/2011 | Fossum et al. |
| 2011/0245138 A1 * | 10/2011 | Kohle .................. C07C 213/06 510/515 |
| 2011/0245140 A1 | 10/2011 | Demeyere |
| 2012/0021959 A1 | 1/2012 | Morgan, III et al. |
| 2012/0328790 A1 | 12/2012 | Nagy et al. |
| 2015/0018515 A1 | 1/2015 | Hosokawa et al. |
| 2015/0126431 A1 * | 5/2015 | Kohle .................. C07C 213/08 510/515 |

FOREIGN PATENT DOCUMENTS

| | | |
|---|---|---|
| DE | 24 30 140 A1 | 2/1976 |
| DE | 34 02 146 A1 | 7/1985 |
| DE | 36 08 093 A1 | 9/1987 |
| DE | 197 08 133 | 12/1997 |
| EP | 0 284 036 | 9/1988 |
| EP | 0 293 955 A2 | 12/1988 |
| EP | 0 302 567 A2 | 2/1989 |
| EP | 0 421 146 A2 | 9/1990 |
| EP | 0 829 531 A1 | 3/1998 |
| EP | 1 018 541 A1 | 7/2000 |
| EP | 1 323 817 A1 | 12/2001 |
| EP | 1 393 706 A1 | 3/2004 |
| EP | 1 584 674 A1 | 10/2005 |
| EP | 1 840 197 A1 | 2/2007 |
| EP | 1 806 392 A1 | 7/2007 |
| GB | 2 007 734 A | 5/1979 |
| GB | 2 039 556 | 8/1980 |
| JP | 2007-009397 | 1/2007 |
| WO | WO 91/01295 | 2/1991 |
| WO | WO 92/18593 | 10/1992 |
| WO | WO 94/14935 | 7/1994 |
| WO | WO 94/19439 | 9/1994 |
| WO | WO 97/42279 | 11/1997 |
| WO | WO 98/38277 | 9/1998 |
| WO | WO 00/06678 | 2/2000 |
| WO | WO 01/32813 A1 | 5/2001 |
| WO | WO 01/42412 A1 | 6/2001 |
| WO | WO 2005/037973 A1 | 4/2005 |
| WO | WO 2005/085404 A1 | 9/2005 |
| WO | WO 2005/095568 A1 | 10/2005 |
| WO | WO 2007/026314 A2 | 3/2007 |
| WO | WO 2007/125005 | 11/2007 |
| WO | WO 2008/003454 A1 | 1/2008 |
| WO | WO 2008/104509 | 9/2008 |
| WO | WO 2009/018955 A2 | 2/2009 |
| WO | WO 2009/099618 A1 | 8/2009 |
| WO | WO 2011/120822 | 10/2011 |
| WO | WO 2011/120836 A1 | 10/2011 |
| WO | WO 2011/123284 A1 | 10/2011 |
| WO | WO 2011/123606 A1 | 10/2011 |
| WO | WO 2011/123733 A1 | 10/2011 |
| WO | WO 2012/061093 A1 | 5/2012 |
| WO | WO 2013/167376 A1 | 11/2013 |

OTHER PUBLICATIONS

Akram, et al., "Synthesis of Tallow Based Esterquat," *J Sci Res* vol. XXX(1):31-36 (Jun. 2010).

Price-Jones, et al.,"1V,N'-ethylenediyl-bis-alkanamides: Differential scanning calorimetry studies," *J. Am. Oil Chem. Soc.* 73:311-319 (Mar. 1996).

Product Advertisement for Tetranyl AO-1, http//kaochemicals-eu.com/213.html, downloaded Jul. 27, 2011.

Ullman's Encyclopedia of Industrial Chemistry; Wiley-VCH Verlag GmbH & Co. KGaA, Weinheim, vol. 14, Table 2, p. 77 (2012).

U.S. Appl. No. 14/398,962, filed Nov. 4, 2014, Köhle.

English language translation of Office Action for corresponding application JP 2014-225357, dated Sep. 25, 2017.

* cited by examiner

METHOD FOR MAKING A TRIS-(2-HYDROXYETHYL)-METHYLAMMONIUM METHYLSULFATE FATTY ACID ESTER

CROSS REFERENCE TO RELATED APPLICATIONS

The present application claims priority to European Application, EP 13191579.5, filed on Nov. 5, 2013, the contents of which is incorporated herein by reference in its entirety.

FIELD OF THE INVENTION

The present invention relates to a method for making a tris-(2-hydroxyethyl)-methylammonium methylsulfate fatty acid ester having a low content of methanol and to fabric softener active compositions obtainable by the method.

BACKGROUND OF THE INVENTION

Quaternary ammonium salts carrying two hydrophobic long chain hydrocarbon moieties have found broad use as fabric softener actives. Quaternary ammonium salts of alkanolamines esterified with on average two fatty acid moieties per molecule, commonly referred to as ester quats, have largely replaced earlier alkyl quaternary ammonium compounds because of their biodegradability.

Tris-(2-hydroxyethyl)-methylammonium methylsulfate fatty acid esters made by quaternizing fatty acid esters of triethanolamine with dimethylsulfate have found broad use as fabric softener actives. Since dimethylsulfate is a potential carcinogen, quaternizing is carried out to achieve complete conversion of dimethylsulfate and a high conversion of amine. It has now been found that tris-(2-hydroxyethyl)-methylammonium methylsulfate fatty acid esters made this way contain unexpectedly high amounts of methanol. Although tris-(2-hydroxyethyl)-methylammonium methylsulfate fatty acid ester softener actives have been in use for more than 20 years, the high content of methanol in these compositions has remained unnoticed.

Since methanol is toxic and presents a workplace hazard, there is therefore a need to provide fabric softener active compositions comprising tris-(2-hydroxyethyl)-methylammonium methylsulfate fatty acid esters which compositions have a low content of methanol. There is also a need for a simple method for making such compositions.

It has now been found that fabric softener active compositions comprising tris-(2-hydroxyethyl)-methylammonium methylsulfate fatty acid esters and having a low content of methanol can be made by quaternizing fatty acid esters of triethanolamine with dimethylsulfate in the presence of a solid acid scavenger.

DESCRIPTION OF THE INVENTION

The present invention is therefore directed to a method for making a tris-(2-hydroxyethyl)-methylammonium methylsulfate fatty acid ester comprising a step of quaternizing a tris-(2-hydroxyethyl)-amine fatty acid ester with dimethylsulfate, wherein the quaternizing is carried out in the presence of a solid acid scavenger.

The invention is further directed to a fabric softener active composition, comprising from 65 to 98% by weight of at least one tris-(2-hydroxyethyl)-methylammonium methylsulfate fatty acid ester, the corresponding non-quaternized tris-(2-hydroxyethyl)-amine fatty acid esters in amounts providing a total amine number of the composition of from 2 to less than 7 mg KOH/g, and from 1 to 1500 ppm methanol.

The method of the invention comprises a step of quaternizing a tris-(2-hydroxyethyl)-amine fatty acid ester with dimethylsulfate in the presence of a solid acid scavenger. The term acid scavenger denotes a material which reacts with a Brönsted acid that is present in the quaternization reaction mixture or that is formed during quaternization, but which material does not react with dimethylsulfate to a substantial extent during quaternization. Preferably, less than 10% of the dimethylsulfate used is consumed by reaction with the acid scavenger, more preferably less than 5% and most preferably less than 2%.

The solid acid scavenger can be a metal carbonate, a metal hydrogen carbonate, a metal oxide, a metal hydroxide, a basic silicate or a basic alumosilicate. The solid acid scavenger is preferably selected from alkali metal carbonates, alkali metal hydrogen carbonates, alkaline earth metal carbonates, alkaline earth metal oxides and alkaline earth metal hydroxides. The alkali metal is preferably lithium, sodium or potassium, most preferably sodium. The alkaline earth metal is preferably magnesium or calcium or a mixture of both. Suitable solid acid scavengers are for example sodium carbonate, sodium hydrogen carbonate, sodium sesquicarbonate, calcium carbonate, magnesium carbonate, dolomite, magnesium hydroxy carbonates, calcium oxide, magnesium oxide, calcium hydroxide or magnesium hydroxide. Most preferably the solid acid scavenger is sodium carbonate or sodium hydrogen carbonate.

The solid acid scavenger is preferably used in an excess to Brönsted acid present in the quaternization reaction mixture and formed during quaternization. More preferably, solid acid scavenger is used in an amount of 1 to 3% by weight, based on the weight of the quaternization reaction mixture.

Carrying out the quaternization of a tris-(2-hydroxyethyl)-amine fatty acid ester with dimethylsulfate in the presence of a solid acid scavenger provides a tris-(2-hydroxyethyl)-methylammonium methylsulfate fatty acid ester having a low content of methanol even at high degrees of quaternization. The method of the invention can therefore provide compositions comprising a tris-(2-hydroxyethyl)-methylammonium methylsulfate fatty acid ester having at the same time a low methanol content and a low total amine number.

The solid acid scavenger preferably consists of particles having a median particle size of at least 100 μm, in particular particles having a median particle size of from 100 μm to 5 mm. The median particle size is determined as the mass-median-diameter of the particle size distribution determined by sieve analysis. Using a solid acid scavenger with the preferred particle size facilitates separation of non-reacted solid acid scavenger from the viscous reaction mixture resulting from quaternization.

The solid acid scavenger is preferably separated by filtration or centrifugation from the reaction mixture resulting from quaternizing. Separating the solid acid scavenger by filtration or centrifugation provides a composition comprising a tris-(2-hydroxyethyl)-methylammonium methylsulfate fatty acid ester containing only small amounts of acidic and basic compounds.

The step of quaternizing can be carried out in the presence of a solvent which is preferably selected from ethanol, 1-propanol, 2-propanol, ethylene glycol, diethylene glycol, propylene glycol, dipropylene glycol, $C_1$-$C_4$-alkyl monoethers of ethylene glycol, $C_1$-$C_4$-alkyl monoethers of propylene glycol and mixtures thereof. However, the step of quaternizing is preferably carried out without addition of a solvent.

In a preferred embodiment of the method of the invention, a solvent selected from ethanol, 1-propanol, 2-propanol, ethylene glycol, diethylene glycol, propylene glycol, dipropylene glycol, $C_1$-$C_4$-alkyl monoethers of ethylene glycol, $C_1$-$C_4$-alkyl monoethers of propylene glycol and mixtures thereof is added to the reaction mixture resulting from quaternizing before separating the solid acid scavenger by filtration or centrifugation. Addition of solvent before filtration or centrifugation facilitates separation of non-reacted solid acid scavenger from the reaction mixture by lowering the viscosity of the mixture. In a further preferred embodiment, the separated solid acid scavenger is washed with this solvent to give a washing liquid and the washing liquid is reused for adding solvent to the reaction mixture resulting from quaternizing. Washing with solvent and reuse of the washing liquid reduces losses of tris-(2-hydroxyethyl)-methylammonium methylsulfate fatty acid ester adhering to the non-reacted solid acid scavenger in the separation by filtration or centrifugation.

The step of quaternizing is preferably carried out with a molar ratio of dimethylsulfate to tris-(2-hydroxyethyl)-amine fatty acid ester of from 0.9 to 0.98, more preferably of from 0.92 to 0.97. The step of quaternizing is preferably carried out at a temperature of from 60 to 95° C., more preferably from 70 to 90° C. Quaternizing may be carried out at any pressure, such as ambient pressure or reduced pressure. Quaternizing is preferably carried out until substantially all of the dimethylsulfate has reacted.

The fatty acid moiety of the tris-(2-hydroxyethyl)-amine fatty acid ester used as a starting material can be derived from a pure fatty acid or a mixture of fatty acids of formula RCOOH, where R is a hydrocarbon group. The hydrocarbon group may be branched or unbranched and preferably is unbranched.

The tris-(2-hydroxyethyl)-amine fatty acid ester may comprise monoesters of formula $N(CH_2CH_2OH)_2(CH_2CH_2OC(=O)R)$, diesters of formula $N(CH_2CH_2OH)(CH_2CH_2OC(=O)R)_2$, and triesters of formula $N(CH_2CH_2OC(=O)R)_3$, where R is the hydrocarbon group of a fatty acid moiety RCOO. The tris-(2-hydroxyethyl)-amine fatty acid ester preferably has an average molar ratio of fatty acid moieties to nitrogen of from 1.4 to 2.0, more preferably of from 1.5 to 1.8. The specified molar ratio provides high softening performance of the quaternized product in a rinse cycle fabric softener.

The fatty acids corresponding to the fatty acid moieties of said tris-(2-hydroxyethyl)-amine fatty acid esters preferably have an iodine value of from 0.5 to 120, more preferably from 1 to 50 and most preferably from 30 to 45. The iodine value is the amount of iodine in g consumed by the reaction of the double bonds of 100 g of fatty acid, determined by the method of ISO 3961.

The fatty acid moieties of the tris-(2-hydroxyethyl)-amine fatty acid esters preferably have an average chain length of from 16 to 18, more preferably of from 16.5 to 17.8 carbon atoms. The average chain length is calculated on the basis of the weight fraction of individual fatty acids in the mixture of fatty acids. For branched chain fatty acids the chain length refers to the longest consecutive chain of carbon atoms.

The preferred iodine values and average chain lengths provide a suitable combination of good processability of the quaternized reaction product in terms of melting point and viscosity and of high fabric softening efficiency in a rinse cycle fabric softener.

In order to provide the required average chain length and iodine value, the fatty acid moieties can be derived from a mixture of fatty acids comprising both saturated and unsaturated fatty acids. The unsaturated fatty acids are preferably monounsaturated fatty acids. The tris-(2-hydroxyethyl)-amine fatty acid ester preferably comprises less than 10% by weight of polyunsaturated fatty acid moieties and more preferably less than 6% by weight. Examples of suitable saturated fatty acids are palmitic acid and stearic acid. Examples of suitable monounsaturated fatty acids are oleic acid and elaidic acid. The cis-trans-ratio of double bonds of unsaturated fatty acid moieties is preferably higher than 55:45 and more preferably higher than 65:35. The fraction of polyunsaturated fatty acid moieties may be reduced by selective touch hydrogenation, which is a hydrogenation that selectively hydrogenates one double bond in a —CH=CH—CH$_2$—CH=CH— substructure but not double bonds of monounsaturated hydrocarbon groups.

The tris-(2-hydroxyethyl)-amine fatty acid ester starting material is preferably prepared by esterifying triethanolamine with a fatty acid or fatty acid mixture, removing the water formed during esterification at reduced pressure. The tris-(2-hydroxyethyl)-amine fatty acid esters made this way can be used without further purification. The desired iodine value, average chain length and molar ratio of fatty acid moieties to nitrogen may be easily adjusted by the choice of fatty acid or fatty acid mixture and the molar ratio of triethanolamine to fatty acid used in the esterification reaction. The esterification is preferably carried out at a temperature of from 160-210° C. at ambient pressure distilling off water until 60 to 80% of the theoretical amount of water has been removed. Then the pressure is reduced stepwise to a final pressure in the range of 5 to 50 mbar and the reaction is continued until an acid value of 1 to 10 mg KOH/g, preferably 2 to 8 mg KOH/g and more preferably 2 to 5 mg KOH/g has been reached.

The method of the invention allows preparing the fabric softener active composition of the invention having a low content of non-quaternized tris-(2-hydroxyethyl)-amine fatty acid ester and a low content of methanol.

The fabric softener active composition of the invention comprises from 65 to 98% by weight of at least one tris-(2-hydroxyethyl)-methylammonium methylsulfate fatty acid ester. The composition further comprises the corresponding non-quaternized tris-(2-hydroxyethyl)-amine fatty acid esters in amounts providing a total amine number of the composition of from 2 to less than 7 mg KOH/g, preferably from 4 to less than 7 mg KOH/g and more preferably from 5 to less than 7 mg KOH/g. The total amine number is determined by non-aqueous titration with perchloric acid according to method Tf 2a-64 of the American Oil Chemists Society and is calculated as mg KOH per g sample.

The fabric softener active composition of the invention also comprises from 1 to 1500 ppm methanol, preferably from 10 to 1000 ppm methanol, more preferably from 10 to 800 ppm methanol, most preferably from 100 to 800 ppm methanol, based on the weight of the composition. This methanol content is lower than in prior art fabric softener compositions containing similar amounts of tris-(2-hydroxyethyl)-methylammonium methylsulfate fatty acid esters and tris-(2-hydroxyethyl)-amine fatty acid esters made by reacting a tris-(2-hydroxyethyl)-amine fatty acid ester with dimethylsulfate. The methanol content of the composition can be determined by head space GLC analysis with calibration by spiking with known amounts of methanol. The fabric softener composition is preferably diluted with a suitable solvent, such as dimethylformamide, to reduce the viscosity for accurate head space GLC analysis. The lower content of methanol in the fabric softener active composition of the invention reduces the need for work safety precautions and the requirements for product labelling and classification and increases the flash point of the composition compared to prior art compositions.

The fabric softener active composition of the invention may further comprise one or more additional organic solvents. The composition preferably comprises up to 35% by weight of a solvent selected from ethanol, 1-propanol, 2-propanol, ethylene glycol, diethylene glycol, propylene glycol, dipropylene glycol, $C_1$-$C_4$-alkyl monoethers of ethylene glycol, $C_1$-$C_4$-alkyl monoethers of propylene glycol and mixtures thereof. The amount of additional solvent is most preferably from 5 to 20% by weight. The more preferred solvents are ethanol, 1-propanol and 2-propanol, most preferably ethanol or 2-propanol and in particular 2-propanol.

The tris-(2-hydroxyethyl)-methylammonium methylsulfate fatty acid ester of the fabric softener active composition of the invention preferably corresponds to a preferred tris-(2-hydroxyethyl)-amine fatty acid ester as defined above as starting material for the method of the invention.

This means that the preferred tris-(2-hydroxyethyl)-methylammonium methylsulfate fatty acid ester can be made by quaternizing a preferred tris-(2-hydroxyethyl)-amine fatty acid ester with dimethylsulfate.

EXAMPLES

Example 1

Methanol Content of Commercial Tris-(2-Hydroxyethyl)-Methylammonium Methylsulfate Tallow Fatty Acid Esters Table 1 shows methanol contents of commercial tris-(2-hydroxyethyl)-methylammonium methylsulfate tallow fatty acid esters determined by head space GC.

TABLE 1

| Methanol content of commercial tris-(2-hydroxyethyl)- methylammonium methylsulfate tallow fatty acid esters | | |
|---|---|---|
| Manufacturer | Product name | Methanol content in ppm |
| Clariant | Praepagen ® TQ | 7000 |
| Stepan | Stepantex ® VA 90 | 3300 |
| Stepan | Stepantex ® VL 85 G | 3800 |
| Stepan | Stepantex ® VK 90 | 3800 |
| Cognis | Dehyquart ® AU 46 | 6100 |
| Cognis | Dehyquart ® AU 57 | 5700 |
| Kao | Tetranyl ® AT 1 | 4600 |
| Rewo | Rewoquat ® V 3620 | 3000 |

Example 2

Preparation of Tris-(2-Hydroxyethyl)-Amine Tallow Fatty Acid Ester

A mixture of 2006 g (6.44 mol) tallow fatty acid having an iodine value of 36 and 632 g (4.26 mol) triethanolamine was heated to 180° C. with stirring, distilling off water from the reaction mixture. After 1 h at this temperature the pressure was reduced stepwise to 10 mbar and the mixture was stirred another 2 h at 180° C. and 10 mbar. The resulting tris-(2-hydroxyethyl)-amine tallow fatty acid ester had an acid value of 7.0 mg KOH/g and a total amine number of 93.7 mg KOH/g.

Preparation of Tris-(2-Hydroxyethyl)-Methylammonium Methyl-Sulfate Tallow Fatty Acid Esters

Example 3

Comparative 111.7 g (0.89 mol) dimethylsulfate was added in small portions with stirring to 563 g (0.94 mol) tris-(2-hydroxyethyl)-amine tallow fatty acid ester from example 2, cooling the reaction mixture to maintain the temperature in the range from 60 to 90° C. After all dimethylsulfate had been added, the reaction mixture was stirred for 1 h at 85° C. Then 75.1 g 2-propanol was added and the mixture was stirred until homogeneous. The resulting composition had a total amine number of 4.6 mg KOH/g and contained 3200 ppm methanol, based on the weight of the composition.

Example 4

92.2 g (0.73 mol) dimethylsulfate was added in small portions with stirring to a mixture of 465.6 g (0.78 mol) tris-(2-hydroxyethyl)-amine tallow fatty acid ester from example 2 and 14 g (0.17 mol) of sodium hydrogen carbonate, cooling the reaction mixture to maintain the temperature in the range from 60 to 90° C. After all dimethylsulfate had been added, the reaction mixture was stirred for 1 h at 85° C. Then 62.0 g 2-propanol was added, the mixture was stirred until homogeneous and filtered with a pressure filter to remove unreacted sodium hydrogen carbonate. The resulting composition had a total amine number of 9.1 mg KOH/g and contained 190 ppm methanol, based on the weight of the composition.

Example 5

Comparative 114.7 g (0.91 mol) dimethylsulfate was added in small portions with stirring to 563 g (0.94 mol) tris-(2-hydroxyethyl)-amine tallow fatty acid ester from example 2, cooling the reaction mixture to maintain the temperature in the range from 60 to 90° C. After all dimethylsulfate had been added, the reaction mixture was stirred for 1 h at 85° C. Then 75.3 g 2-propanol was added and the mixture was stirred until homogeneous. The resulting composition had a total amine number of 3.1 mg KOH/g and contained 4000 ppm methanol, based on the weight of the composition.

Example 6

86.9 g (0.69 mol) dimethylsulfate was added in small portions with stirring to a mixture of 428.9 g (0.716 mol) tris-(2-hydroxyethyl)-amine tallow fatty acid ester from example 2 and 10.6 g (0.13 mol) of sodium hydrogen carbonate, cooling the reaction mixture to maintain the temperature in the range from 60 to 90° C. After all dimethylsulfate had been added, the reaction mixture was stirred for 1 h at 85° C. Then 57.9 g 2-propanol was added, the mixture was stirred until homogeneous and filtered with a pressure filter to remove unreacted sodium hydrogen carbonate. The resulting composition had a total amine number of 6.4 mg KOH/g and contained 1100 ppm methanol, based on the weight of the composition.

Example 7

94.6 g (0.75 mol) dimethylsulfate was added in small portions with stirring to a mixture of 466.6 g (0.78 mol) tris-(2-hydroxyethyl)-amine tallow fatty acid ester from example 2 and 8.6 g (0.147 mol) of magnesium hydroxide, cooling the reaction mixture to maintain the temperature in the range from 60 to 90° C. After all dimethylsulfate had been added, the reaction mixture was stirred for 1 h at 85° C. Then 63.0 g 2-propanol was added, the mixture was stirred until homogeneous and filtered with a pressure filter to remove unreacted sodium magnesium hydroxide. The resulting composition had a total amine number of 6.9 mg KOH/g and contained 610 ppm methanol, based on the weight of the composition.

Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A fabric softener active composition, comprising
   a) from 65 to 98% by weight of at least one tris-(2-hydroxyethyl)-methylammonium methylsulfate fatty acid ester,
   b) the corresponding non-quaternized tris-(2-hydroxyethyl)-amine fatty acid esters in amounts providing a total amine number of the composition of from 2 to less than 7 mg KOH/g, and
   c) from 1 to 1500 ppm methanol.

2. The fabric softener active composition of claim 1, comprising from 10 to 800 ppm methanol.

3. The fabric softener active composition of claim 1, further comprising up to 35% by weight of a solvent selected from the group consisting of ethanol, 1-propanol, 2-propanol, ethylene glycol, diethylene glycol, propylene glycol, dipropylene glycol, $C_1$-$C_4$-alkyl monoethers of ethylene glycol, $C_1$-$C_4$-alkyl monoethers of propylene glycol and mixtures thereof.

4. The fabric softener active composition of claim 1, wherein said tris-(2-hydroxyethyl)-methylammonium methylsulfate fatty acid ester has an average molar ratio of fatty acid moieties to nitrogen of from 1.4 to 2.0.

5. The fabric softener active composition of claim 1, wherein the fatty acid moieties of said tris-(2-hydroxyethyl)-methylammonium methylsulfate fatty acid ester have an iodine value of from 0.5 to 120.

6. The fabric softener active composition of claim 1, wherein the fatty acid moieties of said tris-(2-hydroxyethyl)-methylammonium methylsulfate fatty acid ester have an average chain length of from 16 to 18 carbon atoms.

7. The fabric softener active composition of claim 1, wherein said tris-(2-hydroxyethyl)-methylammonium methylsulfate fatty acid ester comprises less than 10 mol-% polyunsaturated fatty acid moieties.

8. The fabric softener active composition of claim 1, wherein the tris-(2-hydroxyethyl)-methylammonium methylsulfate fatty acid ester is made by a method comprising a step of quaternizing a tris-(2-hydroxyethyl)-amine fatty acid ester with dimethylsulfate, wherein the quaternizing is carried out in the presence of a solid acid scavenger.

9. The fabric softener active composition of claim 8, wherein the solid acid scavenger in said method is selected from the group consisting of alkali metal carbonates, alkali metal hydrogen carbonates, alkaline earth metal carbonates, alkaline earth metal oxides and alkaline earth metal hydroxides.

10. The fabric softener active composition of claim 9, wherein the solid acid scavenger in said method is sodium carbonate or sodium hydrogen carbonate.

11. The fabric softener active composition of claim 8, wherein the solid acid scavenger in said method consists of particles having a median particle size of at least 100 μm.

12. The fabric softener active composition of claim 8, wherein, after quaternizing in said method, the solid acid scavenger is separated by filtration or centrifugation.

13. The fabric softener active composition of claim 12, wherein, in said method, a solvent selected from the group consisting of ethanol, 1-propanol, 2-propanol ethylene glycol, diethylene glycol, propylene glycol, dipropylene glycol, $C_1$-$C_4$-alkyl monoethers of ethylene glycol, $C_1$-$C_4$-alkyl monoethers of propylene glycol and mixtures thereof, is added after quaternizing and before separating the solid acid scavenger.

14. The fabric softener active composition of claim 13, wherein the separated solid acid scavenger is washed with said solvent to give a washing liquid and the washing liquid is reused for adding solvent after quaternizing.

15. The fabric softener active composition of claim 8, wherein the molar ratio of dimethylsulfate to tris-(2-hydroxyethyl)-amine fatty acid ester in said method is from 0.9 to 0.98.

16. The fabric softener active composition of claim 8, wherein quaternizing in said method is carried out at a temperature of from 60 to 95° C.

17. The fabric softener active composition of claim 8, wherein the tris-(2-hydroxyethyl)-amine fatty acid ester in said method has an average molar ratio of fatty acid moieties to nitrogen of from 1.4 to 2.0.

18. The fabric softener active composition of claim 8, wherein the fatty acid moieties of said tris-(2-hydroxyethyl)-amine fatty acid ester in said method have an iodine value of from 0.5 to 120.

19. The fabric softener active composition of claim 8, wherein the fatty acid moieties of said tris-(2-hydroxyethyl)-amine fatty acid ester have an average chain length of from 16 to 18 carbon atoms.

20. The fabric softener active composition of claim 8, wherein the tris-(2-hydroxyethyl)-amine fatty acid ester comprises less than 10 mol-% polyunsaturated fatty acid moieties.

* * * * *